United States Patent [19]

Ballhause et al.

[11] Patent Number: 5,114,935
[45] Date of Patent: May 19, 1992

[54] SUBSTITUTED 6-BENZYL-2H-3,4,5,6-TETRAHYDRO-(1,3)-OXAZINES

[75] Inventors: Helmut Ballhause; Gunther Engelhardt; Claus A. Landgraf; Norbert Mayer; Willy Roth, all of Biberach; Kurt Schumacher, Speyer; Alex Prox, Warthausen, all of Fed. Rep. of Germany

[73] Assignee: Dr. Karl Thomae GmbH, Biberach an der Riss, Fed. Rep. of Germany

[21] Appl. No.: 568,446

[22] Filed: Aug. 15, 1990

[30] Foreign Application Priority Data

Aug. 16, 1989 [DE] Fed. Rep. of Germany ....... 3926898

[51] Int. Cl.⁵ .................. C07D 265/06; A61K 31/535
[52] U.S. Cl. ..................................... 514/228.8; 544/88
[58] Field of Search .................... 544/88; 514/228.8

[56] References Cited

U.S. PATENT DOCUMENTS 4,164,459 8/1979 Noomen et al. .............. 204/159.18

Primary Examiner—John M. Ford
Assistant Examiner—Philip Datlow
Attorney, Agent, or Firm—David E. Frankhouser; Daniel Reitenbach; Mary-Ellen M. Timbers

[57] ABSTRACT

Novel compounds of the general formula

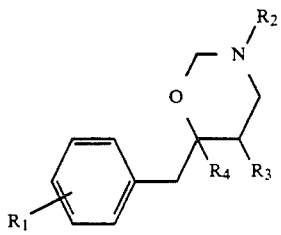

which have antitussive activity, wherein $R_1$–$R_4$ are as defined herein.

18 Claims, 3 Drawing Sheets (+)- AND (-)-ENANTIOMERS OF FIGS 3 AND 4

9.55
10.28
11.22

LC CONDITIONS AS IN FIG. 2

SUBSTITUTED 6-BENZYL-2H-3,4,5,6-TETRAHYDRO-(1,3)-OXAZINES

One of the best known antitussives is the morphine derivative "codeine" with the formula

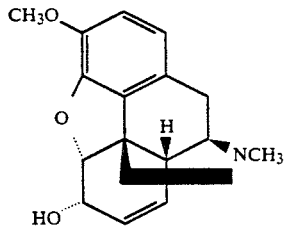

German Patent No. P1146068 describes base-substituted carbinoles of general formula

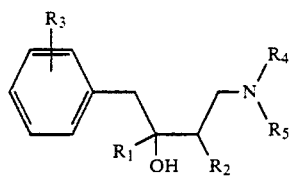

wherein $R_1$ to $R_5$ represent low molecular weight alkyl groups and $R_3$ may be a hydrogen or a p-halogen atom and which may be used as antitussives. One of these compounds, 1-p-chloro-2,3-dimethyl-4-dimethylaminobutanol, has been on the market for some years as a commercial preparation of the Firm Dr Karl Thomae GmbH under the name "Silomat". The substance has the INN generic name "Clobutinol".

The aim of the present invention is to find new compounds which have an antitussive effect but do not have the known unpleasant side affects of codeine.

DESCRIPTION OF THE INVENTION

Figure 2:
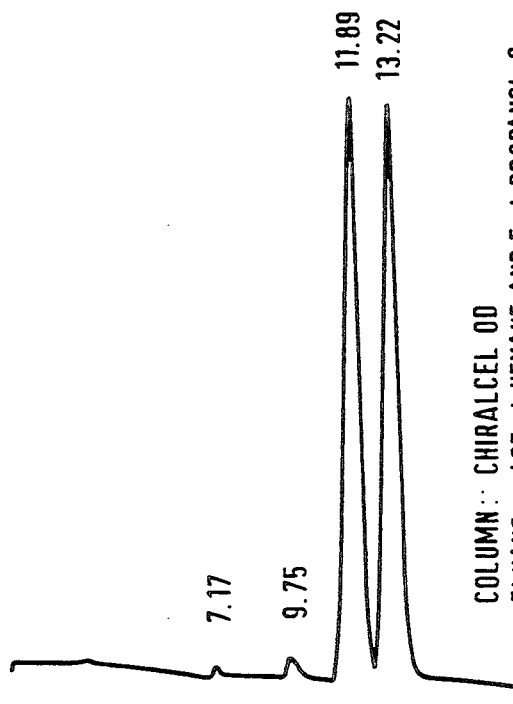
FIG. 2 is a liquid chromatogram of a racemate solution of (±)-6-(p-chlorobenzyl)-3,5,6-trimethyl-2H-3,4,5,6-tetrahydro-(1,3)-oxazine eluted from a Chiralcel OD column using an eluant of hexane and 2-propanol (495:5).

The invention relates to new 1,3-oxazines of general Formula I

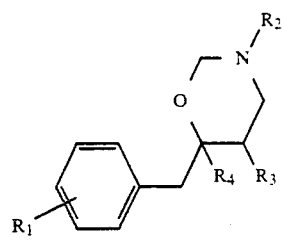

wherein $R_1$ represents a hydrogen or halogen atom, $R_2$ represents a $C_{1-3}$ alkyl group and $R_3$ and $R_4$, which may be identical or different, represent $C_{1-3}$ alkyl groups, the physiologically acceptable acid addition salts thereof with organic or inorganic acids; and processes for preparing them.

Preferred compounds of general Formula I above are those wherein $R_1$ is a halogen atom in the p position.

A compound wherein $R_1$ is a chlorine atom, preferably p-chlorine, and $R_2$ to $R_4$, which may be identical or different, represent methyl or ethyl, is particularly preferred.

The process for preparing these new compounds is characterised in that a compound of general Formula II

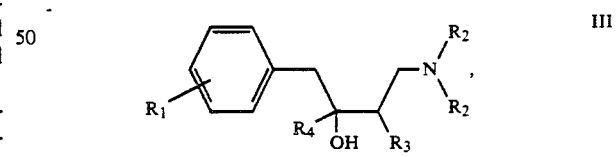

or an acid addition salt thereof is reacted with an aqueous formaldehyde solution, expediently at temperatures between 20° C. and the boiling temperature of the solution, but preferably at ambient temperature, the compound of general Formula I formed initially is isolated by methods known per se. preferably as an acid addition salt thereof, and if desired a free base is converted into an acid addition salt or an acid addition salt is converted into a free base by methods known per se.

The compounds of general Formula II may be prepared for example by the following methods:

a) Mono-de-N-alkylation of a compound of general Formula III

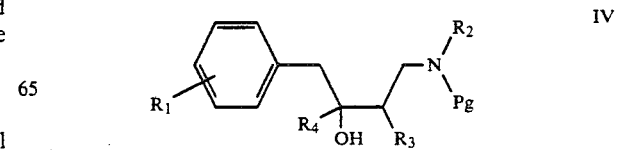

or an acid addition salt thereof, where $R_1$ to $R_4$ are defined as hereinbefore and $R_2'$ represents a methyl group, b) Removal of the protecting group Pg from a compound of general Formula IV or an acid addition salt thereof.

The mono-de-N-alkylation according to process a) may be carried out by methods known per se, e.g. by reacting with diethylazodicarboxylate in a non-polar solvent such as toluene at a temperature up to the boiling temperature of the mixture and hydrolysing the resulting products, preferably with the use of ammonium chloride solution in a polar solvent such as methanol/water at a temperature up to the boiling temperature of the mixture.

Compounds of general Formula III are known from the literature, e.g. from German Patent applications P1146068 and P1153380.

Process b) may be carried out by methods known per se, depending on the identity of the protecting group. The protecting group is preferably the t-butyloxycarbonyl group (Boc) which can be split off by the use of trifluoroacetic acid.

The compounds of general Formula IV may be prepared by methods known per se. Preferably, these intermediate products are produced using compounds of general Formula III as starting materials according to the following reaction plan:

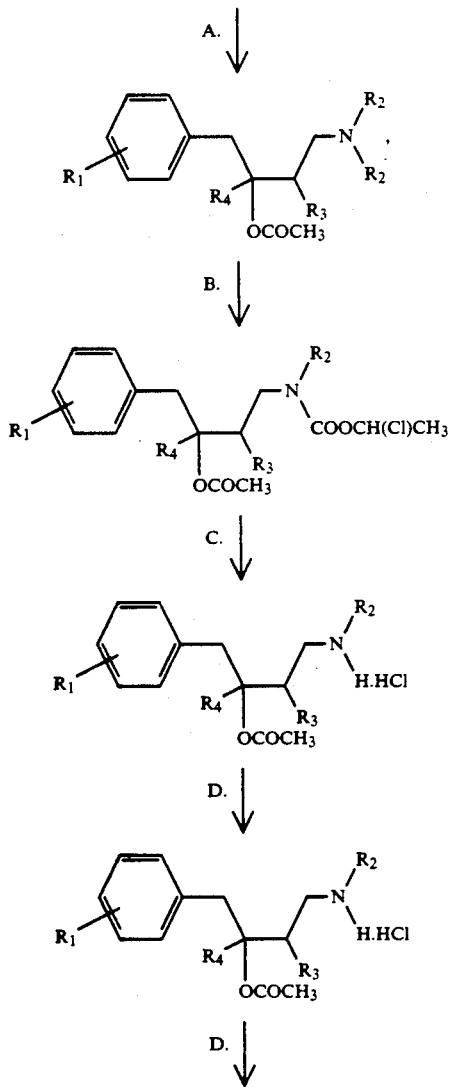

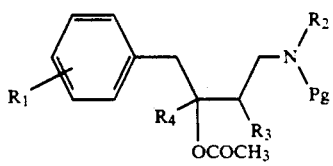

Compounds of Formula IV

In the above reaction sequence a compound of Formula III is reacted with acetyl chloride in an inert solvent, e.g. toluene, at a temperature up to the boiling temperature. Compound V or a hydrochloride salt thereof may be isolated by methods known per se and then stirred with alpha-chloroethyl chloroformate in 1,2-dichloroethane or another suitable organic solvent at a temperature up to the boiling temperature of the mixture and compound VI can be isolated by further processing methods known per se. The resulting compound is then heated to boiling in methanol or another inert solvent. The secondary amine VII thus produced is then precipitated as the hydrochloride, which is isolated and then purified and dried by known methods. The compound VII is then converted into protected amino derivatives by methods known per se. Preferably, this is carried out with Di-t-butyl-di-carbonate in an organic solvent such as dioxane, for example, in the presence of an organic base such as triethylamine at a temperature from 20° C. to the boiling temperature of the mixture, preferably at ambient temperature.

If the compounds of general Formula I obtained have not already been prepared as acid addition salts, they may be converted into the physiologically acceptable acid addition salts with organic or inorganic acids by known methods, e.g. by reacting an alcoholic solution of the base with the equimolar quantity of the corresponding acid in ether. Acids which have proved suitable include hydrochloric, hydrobromic, sulphuric, phosphoric, lactic, citric, tartaric and maleic acids.

The 1,3-oxazines of Formula I are racemates, which can, if desired, be split into their optically active antipodes in the usual way, e.g. with optically active acids, by fractional crystalisation. The compounds according to the invention may be prepared, for example, from the active antipodes of the compounds III, whilst the starting materials of Formula III, for example, may be resolved into their optically active antipodes, e.g. by racemate separation by liquid chromatography and processes a) or b) may be carried out. The intermediate products V to VIII may be treated in the same way if they occur as racemates. The optical purity of the starting or intermediate substances of Formula III, for example, and of the antipodes of the compounds of Formula I claimed may be demonstrated by liquid chromatography on a chiral column (see FIGS. 1 to 5).

For medical use the compounds according to the invention may be incorporated, with the aid of conventional galenic excipients such as lactose, manitol, corn starch, methyl cellulose, hydroxyethyl cellulose, polyethylene oxide, highly dispersed aluminium oxide, magnesium-aluminium silicate, magnesium oxide, magnesium stearate, sodium lauryl sulphate, sodium citrate, tartaric acid, sodium pyrosulphite, dioctylsodiumsulfosuccinate, sodium salt of methyl p-hydroxybenzoate, sodium salt of propyl p-hydroxybenzoate, sodium saccharin, flavourings and antifoamers into conventional galenic preparations such as tablets, film-coated tablets, oblong tablets, coated tablets or capsules and the delayed release forms thereof, ampoules, dry ampoules, dry granules or dry elixirs.

The antitussive activity of the compound 6-(p-chlorobenzyl)-3,5,6-trimethyl-2H-3, 4, 5, 6-tetrahydro-oxazine (1,3)-hydrochloride was tested as follows:

33 male and female cats with a body weight of 3.4 to 4.5 kg were anaesthetised with pentobarbital-Na (45 mg/kg as an initial bolus i.p. and then, spread throughout the experiment, several times as required, 7.5 or 15 mg/kg i.v.). Care was taken to keep the animals at about stage 1 to 2 (Guedel) of the tolerance stage.

Coughing fits were provoked mechanically by the insertion of a plastic catheter with a rounded tip, diameter about 1.5 mm, into the trachea as far as the bifurcation. At each time of irritation, a series of 3 stimuli were carried out at intervals of about 30 seconds. The coughing fits were always provoked 5, 25 and 45 minutes after administration of the test substance or vehicle.

The test substance was administered as a solution in 0.9% NaCl solution through a catheter in the V. femoralis. The injected volume was not more than 0.5 ml/kg. Before administration of the substance, the effect of the vehicle was tested on each animal.

In order to evaluate the cough-suppressing effect, the number of stimuli which did not result in coughing fits were correlated to the total number thereof at each time after administration of the substance and the percentage inhibition was thus calculated (Table 1).

TABLE 1

| Substance | Dosage mg/kg i.v. | n | Percentage inhibition of coughing, MW ± SE after minutes | | |
|---|---|---|---|---|---|
| | | | 5 | 25 | 45 |
| Control | — | 33 | 6.1 ± 3.4 | 5.1 ± 3.2 | 7.1 ± 3.3 |
| Active | 0.5 | 5 | 26.7 ± 8.5 | 16.7 ± 10.5 | 23.3 ± 10.0 |
| substance | 0.705 | 5 | 23.3 ± 6.7 | 13.3 ± 6.2 | 13.3 ± 3.3 |
| | 1.0 | 5 | 33.3 ± 18.3 | 40.0 ± 16.3 | 36.7 ± 3.3 |
| | 1.41 | 5 | 63.3 ± 13.3 | 53.3 ± 16.2 | 50.0 ± 18.3 |
| | 2.0 | 5 | 33.3 ± 17.5 | 53.3 ± 14.3 | 36.7 ± 17.0 |
| | 2.83 | 5 | 36.7 ± 14.3 | 43.3 ± 13.5 | 40.0 ± 11.3 |
| | 4.0 | 5 | 60.0 ± 11.3 | 63.3 ± 13.3 | 46.7 ± 9.7 |
| | 5.64 | 5 | 70.0 ± 20.0 | 70.0 ± 20.0 | 63.3 ± 17.0 |
| | 8.0 | 3 | 44.4 ± 29.4 | 50.0 ± 25.5 | 44.4 ± 20.0 |

By linear regression analysis and linear covariance analysis, the $ED_{50}$ value (50% reduction in the number of coughs) was determined after parallel adjustment (Table 2).

TABLE 2

| Minutes after administration of substance | $ED_{50}$ mg/kg i.v. after parallel adjustment |
|---|---|
| 5 | 2.6 |
| 25 | 2.4 |
| 45 | 3.2 |

The substance, administered intravenously in doses of 0.5 to 8 mg/kg, had the effect of reducing the number of mechanically provoked coughs. The cough-suppressing effect was observed from the lowest administered dose upwards, at every testing time.

The new compounds of general Formula I according to the invention and the physiologically acceptable acid addition salts thereof are suitable, in view of the above mentioned pharmacological properties thereof, as antitussives, particularly for treating coughs in the respiratory tract, whooping cough, irritable and spasmodic coughing.

The dosage required to achieve the effect is conveniently 0.1 to 4.0 mg/kg, preferably 0.3 to 1.5 mg/kg, 2 to 4 times a day.

EXAMPLE 1

6-(p-chloro-benzyl)-3,5,6-trimethyl-2H-3,4,5,6-tetrahydro-oxazine(1,3)-hydrochloride 4.0 g of 1-(p-chloro-phenyl)-2-hydroxy-2,3-dimethyl-4-methylaminobutane hydrochloride were dissolved in 10 ml of water and 10 ml of approx 36% formaldehyde solution were added. After standing for 12 hours at ambient temperature the mixture was made alkaline with conc. ammonia whilst being cooled and the base fractions were extracted with ether. After the ether phase had been dried over sodium sulphate the filtrate was concentrated by evaporation and the oily residue was taken up in a little methanol. The methanolic solution was adjusted to a pH of about 5 with ethereal hydrochloric acid and sufficient ether was added to precipitate the hydrochloride formed. The solution was heated to boiling with ethyl acetate, with partial evaporation of ether and methanol, until the hydrochloride was precipitated. The hydrochloride was suction filtered, decocted with ethyl acetate, filtered and dried.

Mp = 198–200° C., yield: 3.3 g.

If the enantiomers of nor-clobutinol are treated analogously, the enantiomers of the 1,3-oxazine claimed are obtained having the following rotary values:

From (+)-clobutinol → (+)-nor-clobutinol →
(−)-1,3-oxazine-HCl: $[alpha]_{D(589)}^{20}$ = −16.83° (c = 0.303; 1 dm; pure ethanol)

From (−)-clobutinol → (−)-nor-clobutinol →
(+)-1,3-oxazine-HCl: $[alpha]_{D(589)}^{20}$ = +16.6° (c = 0.301; 1 dm; pure ethanol)

Mp = (−)-1,3-oxazine-HCl: 197–199 C
(+)-1,3-oxazine-HCl: 197–199 C

EXAMPLE 2

Tablets containing 5.0 mg of 6-(p-chlorobenzyl)-3,5,6-trimethyl-2H-3,4,5,6-tetrahydro-oxazine-(1,3) -hydrochloride Composition

| Active substance | 5.0 mg |
|---|---|
| Lactose | 148.0 mg |
| Potato starch | 65.0 mg |
| Magnesium stearate | 2.0 mg |
| | 220.0 mg |

Method of Preparation

A 10% mucilage is prepared from potato starch by heating. The active substance, lactose and remaining potato starch are mixed together and granulated with the mucilate through a screen with a mesh size of 1.5 mm. The granules are dried at 45° C., rubbed through the same screen again, mixed with magnesium stearate and compressed into tablets.

EXAMPLE 3

Ampoules containing 10 mg of 6-(p-chlorobenzyl)-
3,5,6-trimethyl-2H-3,4,5,6-tetrahydro-oxazine
(1,3)-hydrochloride Composition

| | |
|---|---|
| Active substance | 10.0 mg |
| Sodium chloride | 8.0 mg |
| Distilled water | ad 1 ml |

Method of Preparation

The active substance and sodium chloride are dissolved in distilled water and topped up to give the required volume. The solution is sterile filtered and transferred into 1 ml ampoules.

Sterilisation: 20 minutes at 120° C.

EXAMPLE 4

Drops containing 0.5 mg of
6-(p-chlorobenzyl)-3,5,6-trimethyl-2H-3,4,5,6-tetrahydro-oxazine (1,3)-hydrochloride per 100.0 ml Composition

| | |
|---|---|
| Methyl p-hydroxybenzoate | 0.035 g |
| Propyl p-hydroxybenzoate | 0.015 g |
| Aniseed oil | 0.05 g |
| Menthol | 0.06 g |
| Pure ethanol | 10.0 g |
| Active substance | 0.5 g |
| Sodium cyclamate | 1.0 g |
| Glycerol | 15.0 g |
| Distilled water | ad 100.0 ml |

Method of Preparation

The active substance and sodium cylamate are dissolved in about 70 ml of water and glycerol is added. The p-hydroxybenzoates, aniseed oil and menthol are dissolved in ethanol and this solution is added to the aqueous solution with stirring. Finally it is topped up to 100 ml with water and filtered to remove any suspended particles.

REFERENCE EXAMPLE 1

1-(p-chlorophenyl)-2-hydroxy-2,3-dimethyl-4-methylaminobutane hydrochloride 26.5 g of clobutinol base are heated to boiling for four hours with 21.0 g of diethyl azodicarboxylate (1.1 molar to clobutinol) in 200 ml of dry toluene. After the toluene has evaporated off in vacuo the residue is hydrolysed for four hours at boiling temperature with 200 ml of methanol and 200 ml of saturated ammonium chloride solution.

The mixture is concentrated by evaporation and the resulting semi-solid residue is mixed with 100 ml of a mixture of equal parts of concentrated hydrochloric acid and water. After suction filtering through a broad filter and re-filtering of the filtrate, the latter is made alkaline with 40% sodium hydroxide solution and ice, and the basic fractions are extracted with ether. The ether phase is separated off and dried over sodium sulphate, then stirred with activated charcoal, filtered and concentrated by evaporation. The concentrated residue is purified by column chromatography on silica gel (0.05 to 0.2 mm) using methylene chloride—methanol—ammonia (940+60+4) to (900+100+6) as eluant. The polar fractions containing the desired nor-clobutinol are combined and the solvent is distilled off. The crude base is converted into the hydrochloride. The basic residue is taken up in a little methanol and neutralised by ethereal hydrochloric acid. The hydrochloride of the desired compound is precipitated. The precipitation is completed by the addition of more ether.

Melting point 182–183° C., about 4.0 g.

Starting from (+) or (−) clobutinol, the corresponding enantiomer of nor-clobutinol is obtained.

REFERENCE EXAMPLE 2

1-(chlorophenyl)-2-hydroxy-2,3-dimethyl-4-methylaminobutane hydrochloride

A. O-acetyl-clobutinol 8.5 ml of acetyl chloride in 20 ml of toluene are added drop wise at 80 C oil bath temperature to 30.0 g of clobutinol base in 150 ml of toluene and the reaction mixture is then heated to boiling for 2 hours. The desired hydrochloride rapidly begins to be precipitated and after cooling of the mixture the hydrochloride is suction filtered, rinsed with ether and dried.

B. N-(aloha-chloroethyl carbamate) of O-acetylnor-clobutinol 16.0 g of O-acetyl-clobutinol base (step A) in 100 ml of 1,2-dichloroethane are heated to boiling for 3 hours with 11.0 g of alpha-chloroethyl-chloroformate in 50 ml of 1,2-dichloroethane. The mixture is then extracted with 1N hydrochloric acid and ice, the organic phase is separated off and extracted under neutral conditions with potassium bicarbonate solution (mixed with ice). The organic layer is separated off, dried over sodium sulphate and the solution is filtered off and evaporated to dryness.

The residue is further processed without any further purification.

C. O-acetyl-nor-clobutinol hydrochloride

The oily residue of the above compound from step B is taken up in 50 ml of methanol and refluxed for 2 hours. The desired hydrochloride starts to be precipitated immediately. Some of the methanol is then distilled off, the mixture is cooled and the crystals are suction filtered. About 10.0 g of hydrochloride are obtained after rinsing with ethyl acetate and drying. MP=185–188° C.

D. O-acetyl-N-Boc-nor-clobutinol 12.8 g of the product of step C are stirred in 500 ml of dioxane together with 10.0 g of di-t-butyl-di-carbonate and 4.0 g of triethylamine for 12 hours at ambient temperature. Then the suspension is suction filtered, filtered and the filtrate is concentrated by evaporation. The residue is further processed without any more purification.

E. N-Boc-nor-clobutinol

The oily residue from step D is refluxed with 50 ml of 1N-sodium hydroxide solution and 100 ml of methanol for 3 hours. Then the methanol is evaporated off in vacuo and the alkaline aqueous suspension is extracted with ether. The ether phase is separated off, dried over sodium sulphate and concentrated by evaporation after it has been filtered. The initially oily residue becomes solid after some time. The solid residue is powdered and used directly for reacting with trifluoroacetic acid.

F. Nor-clobutinol 12.0 g of the above Boc compound from step E are dissolved in 40 ml of ice-cooled trifluoroacetic acid. The reaction solution is left to stand for 30 minutes whilst cooling with ice and for 2 hours at ambient temperature. Then the majority of the trifluoroacetic acid is distilled off at 30° C., the residue is taken up in water and ice and the non-basic fractions are extracted with ether. The aqueous phase is separated off, made alkaline with 40% sodium hydroxide solution whilst cooling with ice, and extracted with methylene chloride. The organic phase is separated off and distilled off and the residue is converted into the hydrochloride. To do this, the oily base is dissolved in a little methanol and ethereal hydrochloric acid is added until the pH is 5. The hydrochloride is then precipitated. Precipitation is completed by the addition of more ether. After suction filtering, the hydrochloride is washed with ethyl acetate. After drying the salt has a melting point of 182-184° C., yield 8.0 g.

REFERENCE EXAMPLE 3

Figure 1:
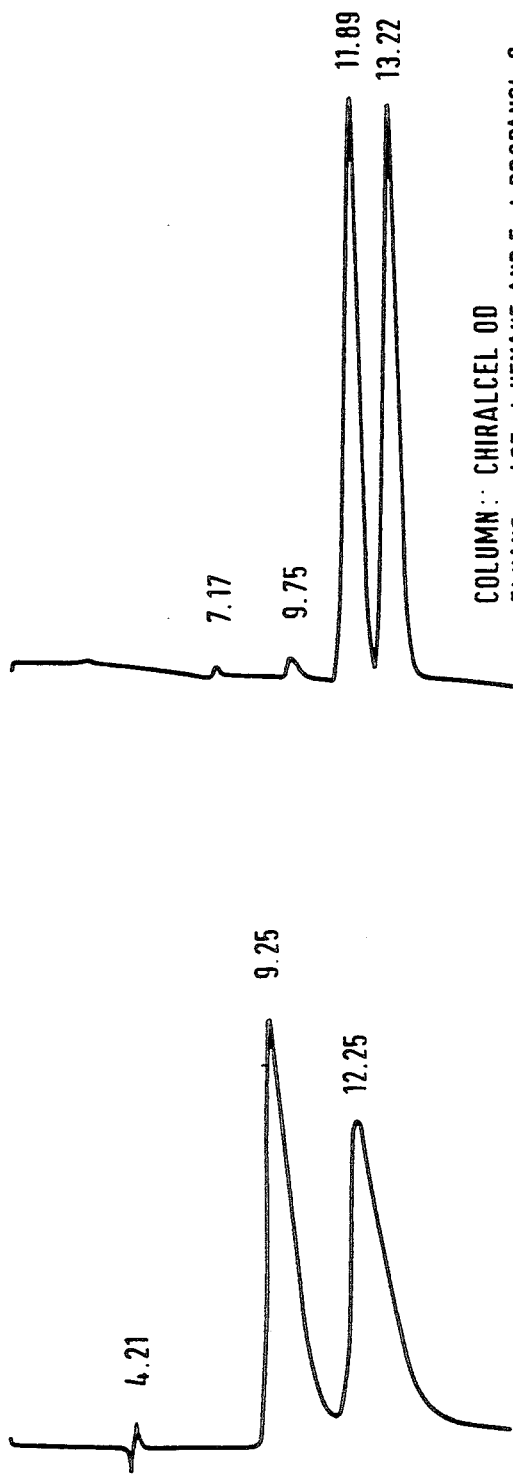
FIG. 1 is a liquid chromatogram of a racemate solution of (±)Clobutinol eluted from a Enantiopac LKB column using an eluant of phosphate buffer (pH 6) and 0.5% 2-propanol.

Analytical demonstration of the optical unity of the I and II enantiomers (A) The racemate (±) 1-p-chlorophenyl-2,3-dimethyl-4-dimethylaminobutan-2-ol is added to an LKB column and eluted with propanol-2 (0.5%) and phosphate buffer, pH 6. As shown in FIG. 1, the (−) enantiomer was obtained after 9.25 minutes and the (+) enantiomer after 12.25 minutes.

(B) The racemate (±) 6-(p-chlorobenzyl)-3,4,5-trimethyl-2H-3,4,5,6-tetrahydro-oxazine(1,3) was added to a chiracel OD column and eluted with 495 ml of hexane and 5 ml of propanol-2. As shown in FIG. 2, the (−) enantiomer was obtained after 11.89 minutes and the (+) enantiomer after 13.22 minutes.

Figure 3:
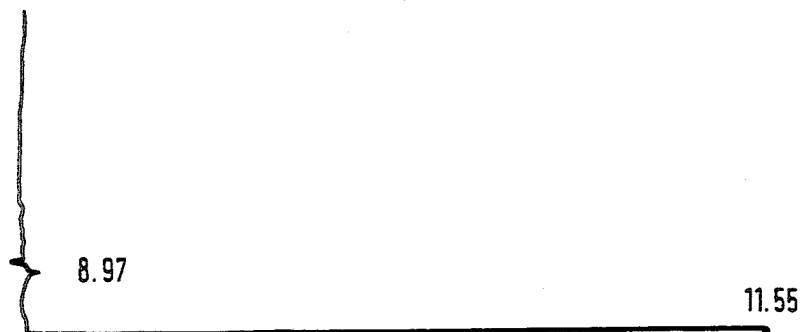
FIG. 3 is a liquid chromatogram of (−)-6-(p-chlorobenzyl) -3,5,6-trimethyl-2H-3,4,5,6-tetrahydro-(1,3)-oxazine eluted from a Chiralcel OD column using an eluant of hexane and 2-propanol (495:5).
Figure 4:
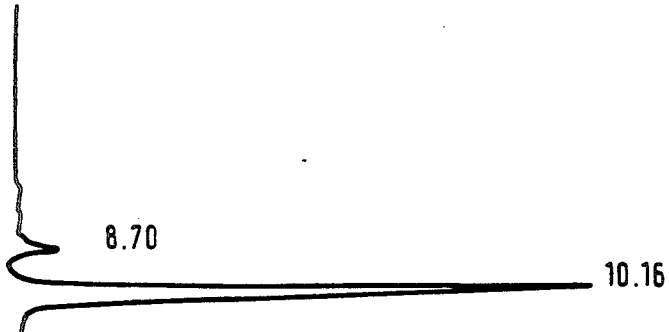
FIG. 4 is a liquid chromatogram of (±)-6-(p-chlorobenzyl) -3,5,6-trimethyl-2H-3,4,5,6-tetrahydro-(1,3)-oxazine eluted from a Chiralcel OD column using an eluant of hexane and 2-propanol (495:5).
Figure 5:
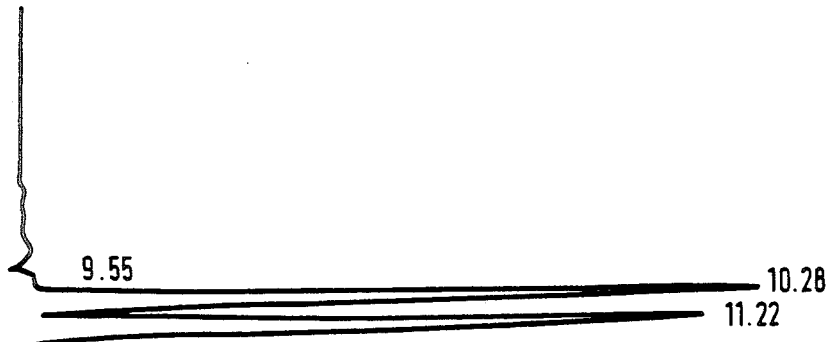
FIG. 5 is a liquid chromatogram of the (+)- and (−) -enantiomers of the compounds in FIGS. 3 and 4 eluted from a Chiralcel OD column using an eluant of hexane and 2-propanol (495:5).

(C) The (+) and (−) enantiomers of the compound 6-(p-chlorobenzyl)-3,5,6-trimethyl-2H-3,4,5,6-tetrahydrooxazine (1,3) were prepared by stereo specific methods using the corresponding (+) and (−) clobutinol as starting material. FIGS. 3 and 4 show the results of the chromatographic analysis of the corresponding products on a chiracel OD column. The (+) and (−) enantiomers of the oxazine were mixed together and also eluted; the results are shown in FIG. 5.

REFERENCE EXAMPLE 4

Test of Binding to the Opiate Receptor

In each experiment, two male rats (about 200 g) were killed by a blow to the neck. Their brains were removed and the brain stem together with the medulla was dissected out and weighed. These tissues were homogenised in 30 ml of 50mM Tris HCl buffer, pH 7.4, using a Potter homogenizer. The resulting homogenised material was centrifuged at 18000xg for 15 minutes.

By subsequent resuspension and centrifugation the pellets were washed twice. The resulting pellets were digested with 200 times their weight of Tris HCl buffer, pH 7.4. In order to match up the binding, 1 ml of this preparation was incubated with 0.5 nM 3H-diprenorphine (38.9 Ci/nmol Amersham), which is a non-selective ligand for the opiate receptors, and the test compound was incubated at varying concentrations in an ice bath.

Incubation was ended after 3 hours and the mixture was rapidly filtered in an "Ismatec Filter-Prep 101 sample processor" using a Whatman GF/B glass wool filter.

The filtrate was rinsed 3 times with 3 ml of carbonised buffer and transferred into small ampulles containing 4 ml of Instasel and extracted overnight. Then the radioactivity was measured. All the measurements were carried out 3 times. Any bound radioactivity found in the presence of 100 nM naloxone was regarded as nonspecific binding.

RESULTS

The radio-labelled opiate-agnostic compound 3H-diprenorphine binds specifically and reversibly to the opiate receptors of the preparations. According to Scatchard analysis, a KD value of 0.51 nM was calculated in a saturation test. The specific binding of 0.5 nM 3H-diprenorphine would be inhibited by naloxone with an IC50 value of 3nM. By contrast to this finding, the test compound shows no inhibition of 3H-diprenorphine up to 100 μM.

What is claimed is:

1. A compound of the formula

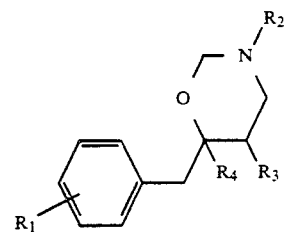

wherein $R_1$ is a hydrogen or halogen atom, $R_2$ is a $C_{1-3}$ alkyl group, and $R_3$ and $R_4$ are each a $C_{1-3}$ alkyl group,
or the physiologically acceptable acid addition salts thereof with an organic or inorganic acid.

2. A compound of the formula

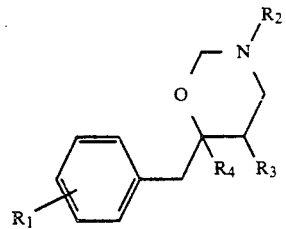

wherein $R_1$ is a halogen atom, $R_2$ is a $C_{1-3}$ alkyl group, and $R_3$ and $R_4$ are each a $C_{1-3}$ alkyl group,
or the physiologically acceptable acid addition salts thereof with an organic or inorganic acid.

3. A compound as recited in claim 2, wherein $R_1$ is in the para position.

4. A compound as recited in claim 2 wherein $R_1$ is a chlorine atom, and $R_2$, $R_3$ and $R_4$ are each a methyl or ethyl group.

5. A compound as recited in claim 2 which is 6-(p-chlorobenzyl)-3,5,6-trimethyl-2H-3,4,5,6-tetrahydro-(1,3)-oxazine, or a physiologically acceptable acid addition salt thereof with an organic or inorganic acid.

6. A compound as recited in claim 5 wherein the organic or inorganic acid is hydrochloric acid.

7. A method for treating coughing in a patient, which comprises administering to the patient an antitussive amount of a compound of the formula

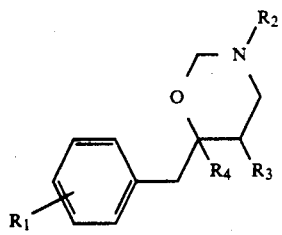

wherein $R_1$ is a hydrogen or halogen atom, $R_2$ is a $C_{1-3}$ alkyl group, and $R_3$ and $R_4$ are each a $C_{1-3}$ alkyl group, or the physiologically acceptable acid addition salts thereof with an organic or inorganic acid.

8. A method for treating coughing in a patient, which comprises administering to the patient an antitussive amount of the compound of claim 2.

9. A method for treating coughing in a patient, which comprises administering to the patient an antitussive amount of the compound of claim 3.

10. A method for treating coughing in a patient, which comprises administering to the patient an antitussive amount of the compound of claim 4.

11. A method for treating coughing in a patient, which comprises administering to the patient an antitussive amount of the compound of claim 5.

12. A method for treating coughing in a patient, which comprises administering to the patient an antitussive amount of the compound of claim 6.

13. A pharmaceutical composition useful for the treatment of coughing which comprises an antitussive amount of the compound of claim 1 and an inert, physiologically acceptable carrier or diluent.

14. A pharmaceutical composition useful for the treatment of coughing which comprises an antitussive amount of the compound of claim 2 and an inert, physiologically acceptable carrier or diluent.

15. A pharmaceutical composition useful for the treatment of coughing which comprises an antitussive amount of the compound of claim 3 and an inert, physiologically acceptable carrier or diluent.

16. A pharmaceutical composition useful for the treatment of coughing which comprises an antitussive amount of the compound of claim 4 and an inert, physiologically acceptable carrier or diluent.

17. A pharmaceutical composition useful for the treatment of coughing which comprises an antitussive amount of the compound of claim 5 and an inert, physiologically acceptable carrier or diluent.

18. A pharmaceutical composition useful for the treatment of coughing which comprises an antitussive amount of the compound of claim 6 and an inert, physiologically acceptable carrier or diluent.

* * * * *